United States Patent [19]

Johnson

[11] 4,192,330
[45] Mar. 11, 1980

[54] HOLDER FOR DENTAL FLOSS

[76] Inventor: Gary D. Johnson, 2 E. 82nd St., New York, N.Y. 10028

[21] Appl. No.: 869,176

[22] Filed: Jan. 13, 1978

[51] Int. Cl.² .............................................. A61C 15/00
[52] U.S. Cl. ...................................................... 132/91
[58] Field of Search ..................................... 132/89–93

[56] References Cited

U.S. PATENT DOCUMENTS

| 1,916,653 | 7/1933 | Bodde | 132/92 R |
|---|---|---|---|
| 2,811,162 | 10/1957 | Brody | 132/89 |
| 3,631,869 | 1/1972 | Espinosa | 132/91 |
| 3,892,249 | 7/1975 | Jones | 132/89 |

FOREIGN PATENT DOCUMENTS 1095460 12/1960 Fed. Rep. of Germany ............. 132/9

*Primary Examiner*—G. E. McNeill
*Attorney, Agent, or Firm*—Bertram Frank

[57] ABSTRACT

A holder for dental floss to be used in conjunction with a disposable cartridge on which the floss is mounted. The holder in one embodiment is an oblong handle having two spaced apart resilient substantially parallel legs which depend from a junction at one end of the handle. The one end of the handle has a bifurcated extension beyond the junction, and portions of the two legs are adjustably engaged with each other so that when the two legs are moved towards each other, the arms of the bifurcated end of the handle are stressed and spread apart from each other. An element including a length of dental floss is mounted on the bifurcated end of the handle so that when the arms are spread apart, the length of dental floss becomes rectilinear. The element typically is a cartridge having a U-shaped resilient frame. The length of dental floss extends between the opposed ends of the frame. In another embodiment, the length of dental floss extends between the ends of the arms of the bifurcated end of the handle and the arms are stressed away from each other so that the arms are spread apart and the length of dental floss becomes stressed and rectilinear.

7 Claims, 17 Drawing Figures

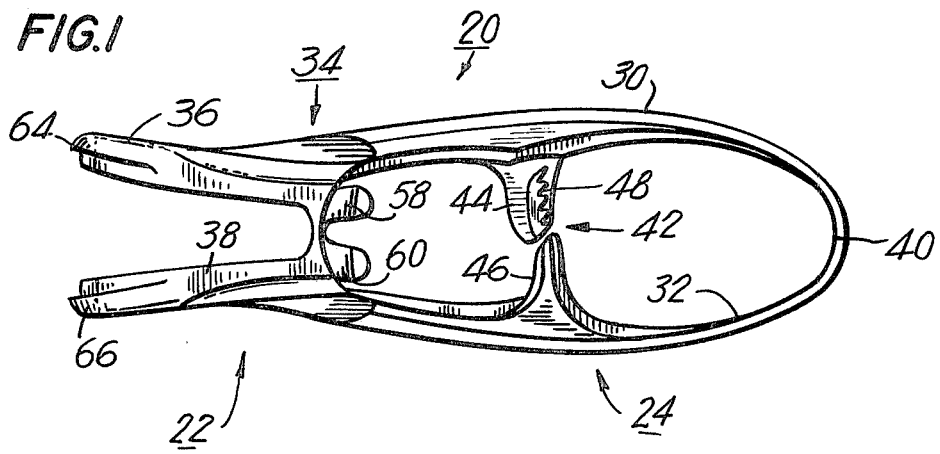
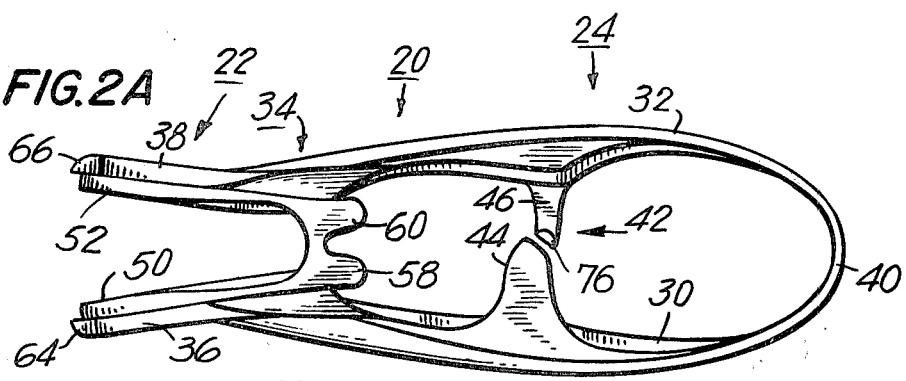
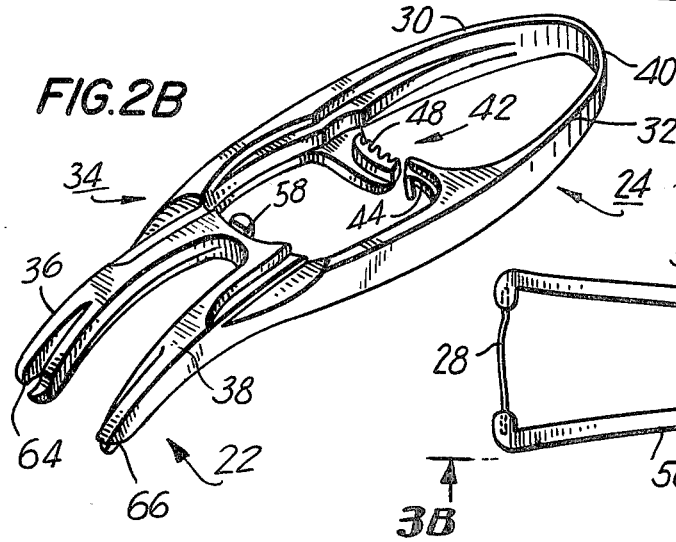
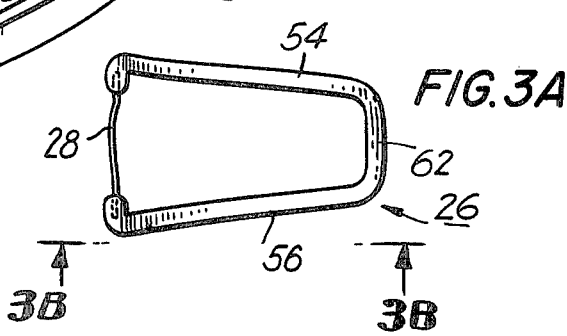

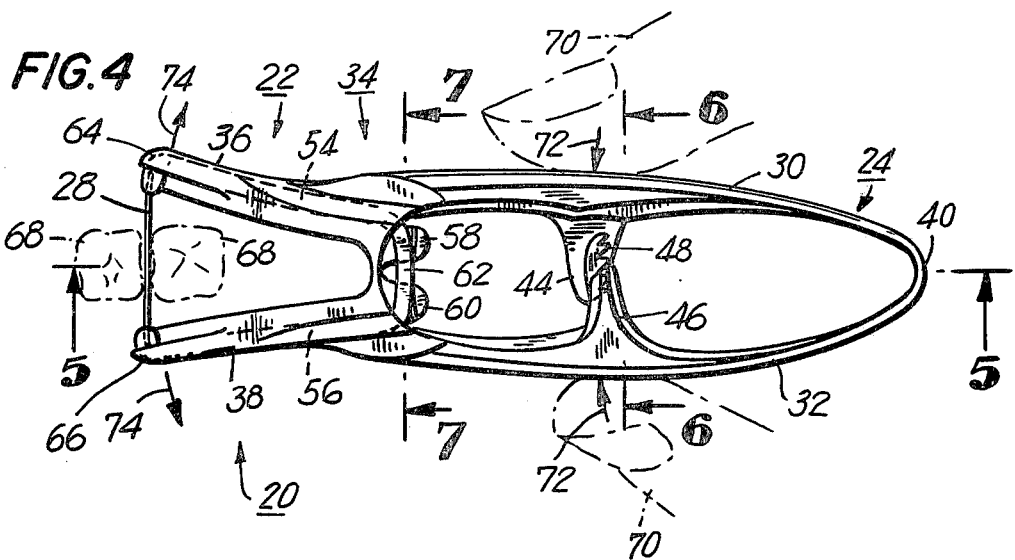
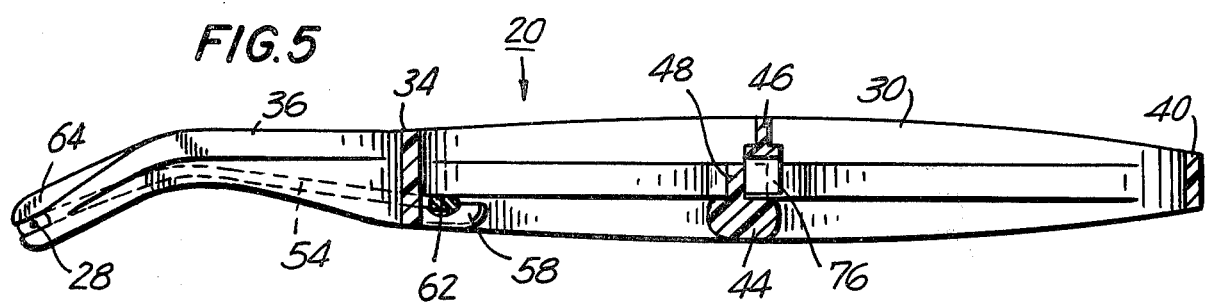
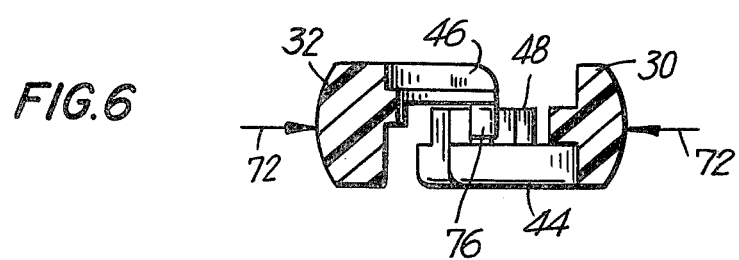
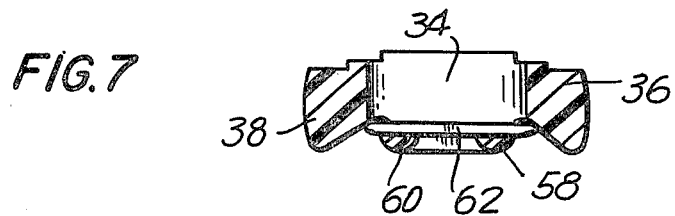

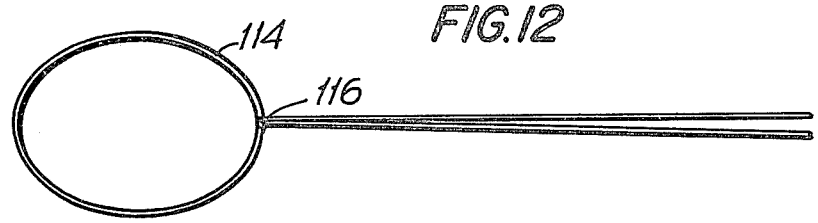
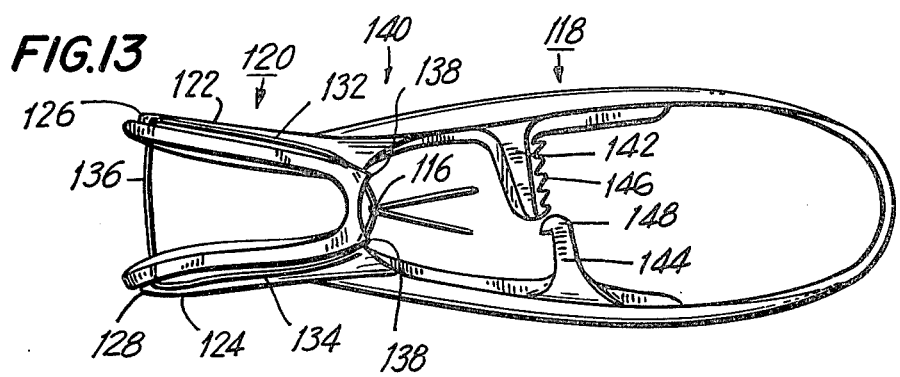
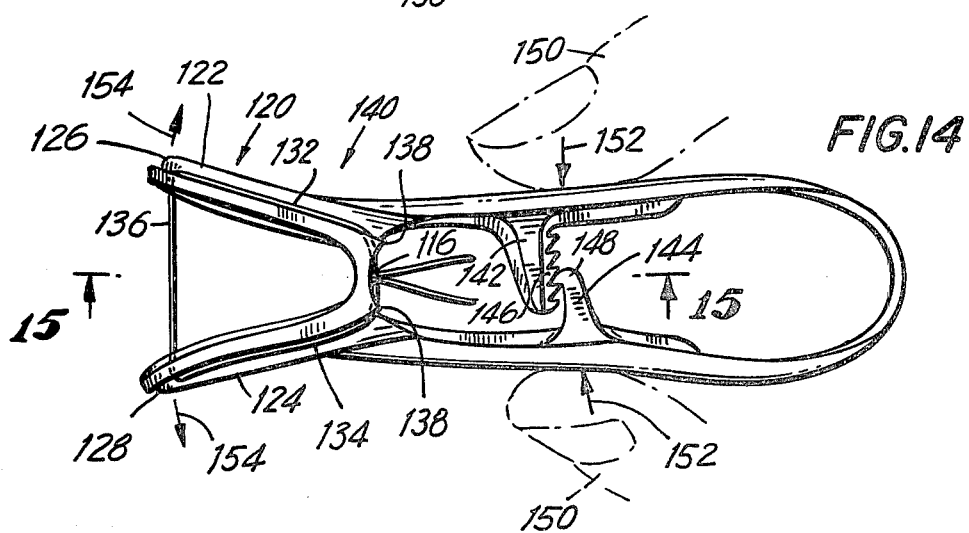
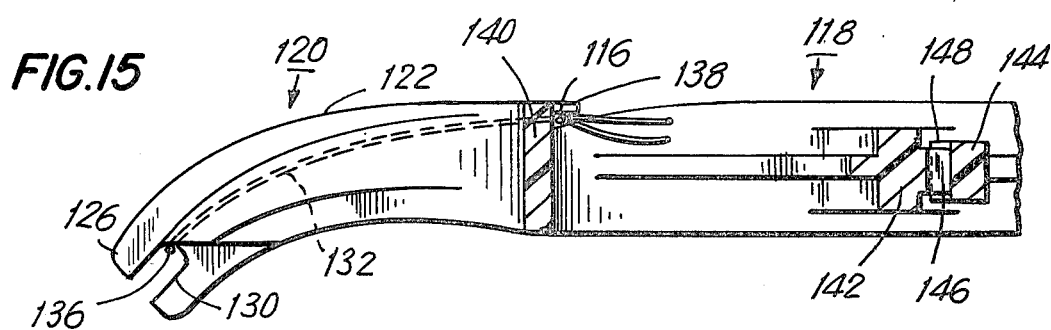

HOLDER FOR DENTAL FLOSS

BACKGROUND OF THE INVENTION

1. Field of the Invention

A holder for dental floss.

2. Description of the Prior Art

It is well known that as part of the regular care of teeth, the use of dental floss to remove food particles from between the teeth is highly recommended by the dental profession. Dental floss is sold in drug stores and elsewhere as a roll of floss which is unwound and cut into a length of dental floss resembling a length of thread, which is then applied to the teeth of the user by winding ends of the length of floss about two fingers, one of the right hand and the other of the left hand, manually stressing the free portion of the floss to a rectilinear configuration, and manipulating the floss between the teeth. This practice is wasteful of floss since the terminal ends of the length of floss are not used. In addition, at least one of the fingers of the user must be inserted into the mouth which is untidy and unsanitary, e.g. the finger becomes coated with saliva.

Thus holders for dental floss, especially in conjunction with a toothbrush, have been suggested in the prior art. In this case the handle of the oblong holder is grasped by the user, and the end of the holder on which the floss is mounted is inserted into the mouth. The holder is then manipulated to urge the dental floss between the teeth. Among the prior art relating to dental floss holders may be mentioned U.S. Pat. Nos. 3,378,017; 3,106,216; 2,784,722; 2,516,539; 2,233,936; 2,176,069; 2,113,439; 2,067,692; 2,029,031; 1,700,690 and 301,055.

SUMMARY OF THE INVENTION

1. Purposes of the Invention

It is an object of the present invention to provide an improved holder for dental floss.

Another object is to provide a holder for dental floss in conjunction with a disposable cartridge, the cartridge holding a length of dental floss and being mountable on the holder.

A further object is to provide an improved article of manufacture for the cleaning of teeth.

An additional object is to provide a simple and inexpensive holder for dental floss which may be mass produced at low cost.

Still another object is to provide a dental floss holder which may be manipulated to stress a length of dental floss mounted to the holder into a rectilinear configuration.

An object is to provide a disposable cartridge holding a length of dental floss which is mountable on the end of an oblong holder for dental floss.

An object is to provide a unitary one piece dental floss holder preferably composed of plastic, which is of reduced bulk and improved efficiency.

An object is to provide a dental floss holder which provides leverage and improves accessibility to least accessible teeth.

An object is to provide a dental floss holder which may be manipulated to tighten the floss and further manipulated to remove tension allowing a cartridge in which the floss is mounted to be replaced.

An object is to provide a cartridge for a holder for dental floss which may be individually wrapped and sanitized, and in which the floss is an integral part of the cartridge.

An object is to provide a dental flossholder with disposable cartridge holding an individual charge of a length of dental floss.

These and other objects and advantages of the present invention will become evident from the description which follows.

2. Brief Description of the Invention

In one embodiment of the present invention, the dental floss holder is characterized by the provision of a plastic handle having two cooperating inner tongues provided with serrations, as well as a forked or bifurcated end for receiving a plastic floss holder or cartridge. The floss cartridge is a disposable item which is attached to the handle, e.g., snapped into place, while the serrated tongues are not engaged. This permits the bifurcated end of the handle to contract when a fresh cartridge is being inserted onto the handle. Then the handle is squeezed to permit the serrations of the tongues to become engaged, which stresses the forked or bifurcated end of the handle outwards so that the two arms of the bifurcated end of the handle tend to move apart, thus holding the cartridge firmly in place so that the device may be employed to clean the teeth. The handle is a one-time purchase item while as mentioned supra the cartridge is a disposable item, i.e., when the floss becomes frayed through usage, the tongues on the handle are manually disengaged by simply spreading the handle sides or legs apart, or by completely crushing the handle in another embodiment. Thereafter, the cartridge is removed and a fresh cartridge is mounted on the handle or holder. A central tab may be provided on the handle adjacent a central curved junction region of the holder, so that the holder may be more firmly snapped into place.

The embodiment of the invention described supra may be summarized as entailing the provision of a holder for dental floss including an oblong handle having two spaced apart resilient generally parallel legs, which legs depend from a junction at one end of the handle. The one end of the handle has a bifurcated extension beyond the junction. Adjustable means are provided to engage portions of the two legs with each other so that when the two legs are moved towards each other, the arms of the bifurcated one end of the handle are stressed and spread apart from each other. A cartridge or other means mountable on the bifurcated one end of the handle is provided, the mountable means including a length of dental floss so that when the aforementioned arms are stressed and spread apart, the length of dental floss becomes stressed and rectilinear and thus may be inserted between two juxtaposed teeth.

The adjustable means to engage the portions of the two legs preferably includes at least one pair of opposed tongues, each of the tongues extending inwards and towards the other tongue from a leg of the handle and each being generally perpendicular to its respective leg. At least one of the tongues is provided with serrations, so that the tongues engagingly cooperate with each other to hold the legs toward each other, and thereby to spread apart the arms, when the legs are moved towards each other. In a preferred embodiment, one tongue is serrated and the other tongue is provided with a terminal lip, which lip engages the serrations on the one tongue when the legs are moved towards each other. The lip in one specific embodiment is offset laterally from the terminus of its tongue, so that the pair of tongues may be disengaged from each other by laterally displacing the one tongue relative to the other tongue.

The legs are preferably joined at the other end of the handle, for greater strength and rigidity of the unit. Preferably the arms are arcuate, both of the arms curving in the same direction away from the junction and out of the plane of the handle. Typically the adjustable means to engage portions of the two legs are disposed proximately in the middle portions of the two legs. In one embodiment of the invention, the means mountable on the bifurcated one end of the handle is simply a loop of dental floss.

In a preferred embodiment, the means mountable on the bifurcated or forked one end of the handle is a cartridge consisting essentially of a generally U-shaped resilient frame and a length of dental floss, which length of dental floss extends generally rectilinearly between the opposed ends of the frame. Each end of the length of dental floss is preferably insert molded into its respective end of the frame, although other modes of engagement such as merely tying each end of the length of dental floss to its respective end of the frame may be adopted, typically by providing a hole in each end of the frame through which the end of the floss length extends for a looped attachment. Typically each of the arms of the bifurcated extension of the handle is grooved on one side, both arms being grooved on the same side, so that the sides of the frame fit into the grooves. In this case the terminus of each arm of the bifurcated one end of the handle may be provided with a tab at or adjacent the junction, so that the resilient frame may be snap fitted into the grooves.

Both the arms of the bifurcated one end of the handle and the sides of the frame of the cartridge are preferably curved; with both of the arms curving in the same direction away from the junction and out of the plane of the handle, and with both sides of the frame curving in the same direction out of the plane of the base of the frame. In this case the aforementioned grooves may be disposed either on the convex outer curvature of the arms or on the concave inner curvature of the arms.

As mentioned supra, the preferred cartridge for the oblong holder for dental floss is a unitary disposable item. In this case the holder will have a bifurcated end and the cartridge is mountable on the bifurcated end of the holder. The disposable cartridge generally consists in most instances of a substantially U-shaped resilient frame and a length of dental floss, with the length of dental floss extending generally rectilinearly between the opposed ends of the frame. The sides of the frame preferably are arcuate, withboth sides of the frame curving in the same direction out of the plane of the base of the frame.

In another and more general embodiment of the invention, the dental floss holder includes an oblong handle having a bifurcated one end and a length of dental floss which extends generally rectilinearly between proximately the ends of the arms of the bifurcated one end of the handle. Each end of the length of dental floss is attached to one of the arms. Means are provided to stress the arms away from each other, so that the arms are spread apart and the length of dental floss becomes stressed and rectilinear. Each end of the length of dental floss is usually insert molded into its respective arm. The arms are preferably arcuate, both of the arms curving in the same direction and out of the plane of the handle.

In this embodiment of the invention, the arms are typically stressed away from each other by means including a panel which is mounted between the arms on collapsible mounting means. The panel is wedge shaped, so that collapsing of the collapsible mounting means wedges the panel towards the one end of the handle and thereby stresses the arms away from each other. The sides of the panel adjacent the arms, and the inner edges of the arms, are preferably serrated, so that wedging of the panel locks the panel and the arms together. In a preferred embodiment, a plurality of spaced apart tabs are provided along the inner edges of the arms. The tabs define opposed channels along the inner edges of the arms. The panel is receivable into the channels when the collapsible mounting means is collapsed. The collapsible mounting means is typically a thin rod which extends from the apex of the panel to the one end of the handle, i.e. the rod extends to the central junction or apex of the bifurcated one end of the handle.

In this latter embodiment of the invention, the dental floss holder per se is a disposable item to be sold as a unitary article of manufacture without auxiliary cartridges.

The present dental floss holder provides several salient advantages. The improved holder is, in one embodiment, a onetime purchase item, to be used in conjunction with a cheap disposable cartridge. The holder is simple and inexpensive and may be mass produced at low cost. The length of dental floss is stressed into a rectilinear configuration, and thus the cleaning efficiency of the article is improved over prior art configurations. In other words, the present holder is of reduced bulk and improved efficiency. The present dental floss holder provides leverage and improves accessibility to least accessible teeth. The present holder may be manipulated to tighten the floss, and further manipulated to remove tension, allowing a cartridge in which the floss is mounted to be replaced. The holder may be individually wrapped and sanitized, and similar considerations apply to the cartridge of which the floss is an integral part. The holder and cartridge are cheaply made from inexpensive plastic such as styrene, nylon, polyvinyl chloride, polyethylene, polypropylene, polyvinyl acetate, methyl methacrylate, or from other materials of construction such as a metal, e.g. steel, aluminum, brass, etc., or from synthetic rubber such as neoprene or buna-S. The preferably insert molded floss can be regular dental floss as is known to the art, deno-floss (tape), flavored or even treated with an anti-bacterial agent.

The invention accordingly consists in the features of construction, combination of elements and arrangement of parts which will be exemplified in the article of manufacture hereinafter described and of which the scope of application will be indicated in the appended claims.

BRIEF DESCRIPTION OF THE DRAWINGS

In the accompanying drawings in which are shown several of the various possible embodiments of the invention:

FIG. 1 is a plan view of one embodiment of dental floss holder of the present invention;

FIG. 2A is a bottom plan view of the dental floss holder of FIG. 1;

FIG. 2B is a perspective view of the dental floss holder of FIGS. 1 and 2;

FIG. 3A shows a cartridge in plan view;

FIG. 3B shows the cartridge of FIG. 3A in elevation view and is an elevation view taken substantially along the line 3B—3B of FIG. 3A;

FIG. 4 shows the mode of emplacement of the cartridge of FIG. 3 onto the bifurcated one end of the dental floss holder of FIGS. 1 and 2, as well as application of the device in service between two juxtaposed teeth;

FIG. 5 is a sectional elevation view taken substantially along the line 5—5 of FIG. 4;

FIG. 6 is a sectional elevation view taken substantially along the line 6—6 of FIG. 4;

FIG. 7 is a sectional elevation view taken substantially along the line 7—7 of FIG. 4;

FIG. 12 shows a loop of dental floss;

FIG. 13 shows the loop of dental floss of FIG. 12 as mounted on another alternative embodiment of dental floss holder in plan view;

FIG. 14 shows the mode of tightening the loop of dental floss on the holder; and FIG. 15 is a partial sectional elevation view taken substantially along the line 15—15 of FIG. 14.

DETAILED DESCRIPTION OF THE PREFERRED EMBODIMENTS

Figure 8:
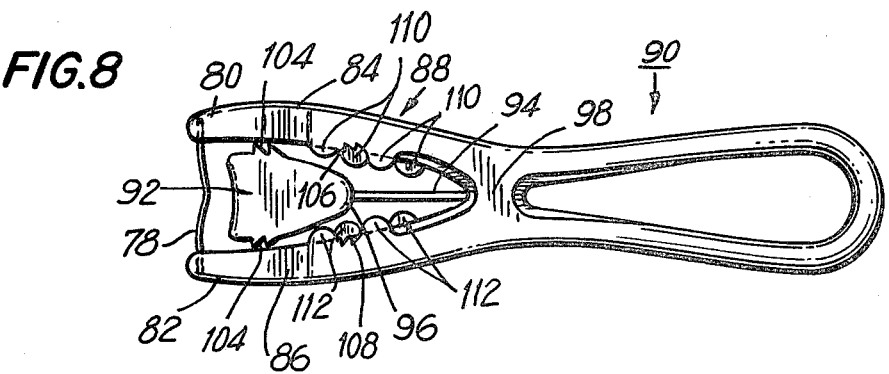
FIG. 8 shows an alternative embodiment of the invention as manufactured for sale as a unitary dental floss holder with in situ floss.

Referring now to FIGS. 1 and 2, a dental floss holder 20 having a bifurcated one end 22 on which a cartridge is mountable is shown. The holder 20 is characterized by having one piece handle 24 preferably composed of nylon, to reduce bulk and improve efficiency. The handle 24 is typically formed in a two plate mold which does not require cams. The function of the handle 24 is to provide leverage and improve accessibility to the least accessible teeth. Crushing the handle 24, with floss cartridge 26 (FIG. 3) inserted, tightens the floss 28. As will appear infra, completely squeezing or crushing the handle will remove this tension, allowing the cartridge to be replaced. The dental floss cartridge 26 is typically composed of styrene with deno-floss 28 (tape) insert molded. The floss 28 becomes an integral part of the cartridge 26, and in practice for commercial sales each cartridge is individually wrapped and sanitized. The insert molded floss 28, as mentioned supra, can be regular floss, deno-tape, flavored, or even treated with an anti-bacterial agent. As an alternative, dental floss loops (supplied pre-tied and sanitized) can also be used as a cartridge. Excess floss is used to facilitate rotation of the loop during use.

The dental floss holder 20 is characterized by the provision of the oblong handle 24 having two spaced apart resilient substantially parallel legs 30 and 32 which depend from a junction 34 at one end of the handle 24. This one end of the handle 24 has the bifurcated extension 22 beyond the junction 34, which extension 22 has two arms 36 and 38. The handle 24 is completed in this embodiment of the invention by the provision of a tension spring end 40 which joins the legs 30 and 32 at the other end of the handle 24 (opposite to the bifurcated end 22), and a locking mechanism 42. The tension spring end 40 tends to hold the legs 30 and 32 apart. The locking mechanism 42 constitutes adjustable means to engage portions of the two legs 30 and 32 with each other when the two legs 30 and 32 are manipulated and moved towards each other (FIG. 4). The locking mechanism 42 in this embodiment of the invention consists of a pair of opposed tongues 44 and 46. Each of the tongues 44 or 46 extends inwards towards the other tongue from a leg 30 or 32 of the handle 24 and each tongue is generally perpendicular to its respective leg. The tongue 44 is provided with serrations 48, so that the tongues 44 and 46 engagingly cooperate with each other as shown in FIGS. 4–6, to hold the legs 30 and 32 toward each other, when the legs 30 and 32 are manipulatively moved towards each other.

The arms 36 and 38 of the bifurcated end 22 are each provided with an inner groove or channel 50 or 52 respectively, which grooves 50 or 52 receive the cartridge 26 when the cartridge 26 is emplaced and mounted on the bifurcated end 22. Both arms 36 and 38 are grooved on the same side, so that the sides 54 and 56 of the frame of the cartridge 26 fit into the respective groove 50 and 52. The grooves 50 and 52 in this embodiment of the invention are disposed on the inner or concave curvature or side of the arms 36 and 38.

The FIGS. 1 and 2 embodiment of the invention is completed by the provision of two tabs 58 and 60 at the inner terminus of each arm 36 or 38 at or adjacent the junction 34, so that the resilient frame of the cartridge 26 may be snap fitted into the grooves 50 and 52, i.e. the sides 54 and 56 fit into the grooves 50 and 52 while base 62 of the frame of the cartridge 26 snaps over the tabs 58 and 60. The cartridge 26 is thus receivable and mountable on the bifurcated end 22 by initially contacting the floss 28 end of the cartridge 26 with the points or free ends 64 and 66 of the respective arms 36 and 38, pivoting the cartridge 26 so that the sides 54 and 56 fall into the respective grooves 50 and 52, and snap fitting the base 62 over the tabs 58 and 60.

The cartridge 26 thus basically entails a generally U-shaped resilient frame having sides 54 and 56 and base 62, together with a length 28 of dental floss which extends generally rectilinearly between the opposed free ends of the frame sides 54 and 56. In this embodiment of the invention, the frame is arcuate as shown in FIG. 3B, with both sides 54 and 56 of the frame curving in the same direction out of the base 62 of the frame. Similarly, both of the arms 36 and 38 are arcuate, with both arms 36 and 38 curving in the same direction away from the junction 34 and out of the plane of the handle 24.

FIG. 4 shows the mode of tensioning of the cartridge 26 on the bifurcated end 22 of the dnetal floss holder 20, as well as the mode of application of the length of floss 28 to teeth 68, which mode of application is well understood by the layman as well as by those skilled in the art. In other words, the stressed and rectilinear length of dental floss 28 is inserted between the teeth 68 to remove food particles, plaque, etc., and thus to prevent tooth decay, by manual manipulation of the holder 20 after the cartridge 26 is in place on the holder. The cartridge 26, after being emplaced on the bifurcated end 22 of the holder 20 as described supra, is stressed in place, so as to stress the length of dental floss 28 and render it rectilinear, by the fingers 70 shown in phantom outline. Each finger 70 presses or squeezes against the sides or legs 30, 32 of the handle 24 of the holder 20 in the direction indicated by arrows 72, so that the legs 30 and 32 are moved closer together, end 40 is placed under spring tension, and tongues 44 and 46 are engaged. The inward stressing of legs 30 and 32 concomitantly stresses arms 36 and 38 outwards and away from each other, via stress on junction 34 and in the direction indicated by arrows 74, so that the cartridge 26 is held firmly in place with the sides 54 and 56 being spread apart, and so that the length of dental floss 28 being stressed into a rectilinear configuration.

FIG. 5 shows the preferred arcuate configuration of the arms 36 and 38, with both of these arms 36 and 38 curving in the same direction out of the plane of the handle 24. FIGS. 5 and 6 show the mode of engagement of the tongues 44 and 46. The tongue 46 is provided with a terminal lip 76, which lip 76 engages the serrations 48 when the legs 30 and 32 are moved towards each other. The lip 76 is offset laterally from the terminus of the tongue 46, as best seen in FIG. 6, so that the pair of tongues 44, 46 may be disengaged from each other by laterally displacing the one tongue 44 relative to the other tongue 46, or by completely squeezing the resilient legs 30, 32 very close to each other in the direction indicated by arrows 72, so that the lip 76 moves inwards past the serrations and is freed from engagement. Thus completely squeezing or crushing the handle will remove the tension on arms 36, 38, allowing the cartridge 26 to be replaced with a fresh cartridge when the length of dental floss 28 becomes frayed or broken through continued usage. FIG. 7 shows how the cartridge base 62 is retained by the tabs 58, 60.

FIGS. 8, 9, 10 and 11 illustrate an alternative embodiment of the invention in which a length of dental floss 78 extends generally rectilinearly between proximately the ends 80, 82 of the arms 84, 86 of the bifurcated one end 88 of the oblong handle 90. Each end of floss length 78 is insert molded or otherwise attached to one end 80 or 82. In this embodiment of the invention, means different from that described supra is preferably provided to stress the arms 84, 86 away from each other, although it will be understood that the means described supra entailing the provision of tongues 44, 46 may alternatively be employed for this purpose. In any event, the means stresses the arms 84, 86 away from each other so that these arms are spread apart and the length of dental floss 78 becomes stressed and rectilinear for the reasons and purposes described supra.

In this embodiment of the invention, the arms 84, 86 are stressed away from each other by means including a wedge shaped panel 92 which is mounted between the arms 84, 86 on collapsible mounting means consisting of a rod 94 which extends from the apex 96 of the panel 92 to junction 98 at one end of the handle 90, which junction 98 is the region where the arms 84, 86 converge and join the handle 90. Manual collapsing of the collapsible mounting means, by the application of force in the direction indicated by arrow 100 (FIG. 9), wedges the panel 92 towards the junction 98 and thus stresses the arms 84, 86 away from each other in the direction indicated by arrows 102, so that the length of dental floss 78 becomes stressed and rectilinear as shown in FIG. 9.

Figure 9:
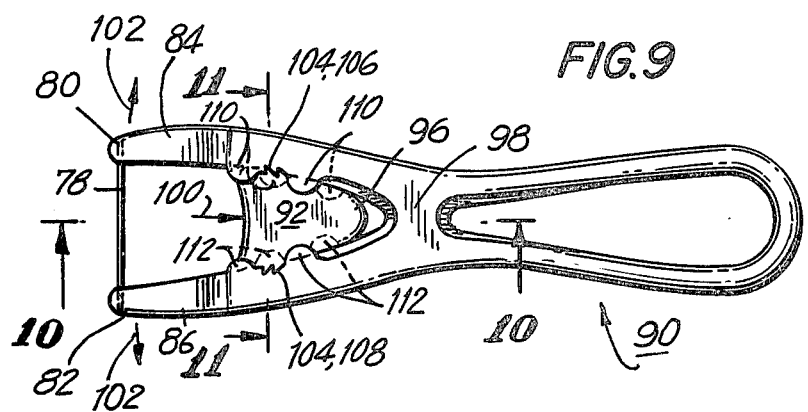
FIG. 9 shows the mode of placing the holder of FIG. 8 in service.
Figure 10:
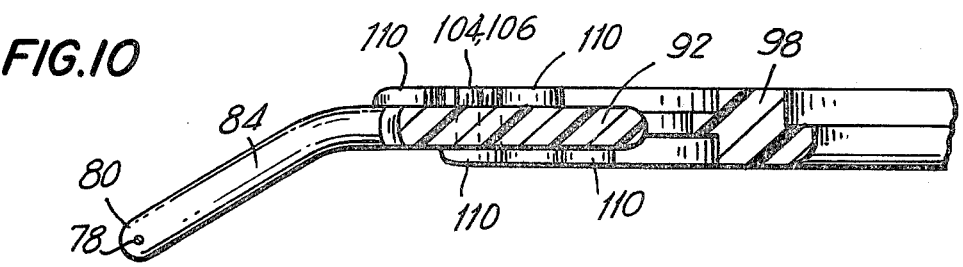
FIG. 10 is a partial sectional elevation view taken substantially along the line 10—10 of FIG. 9.
Figure 11:
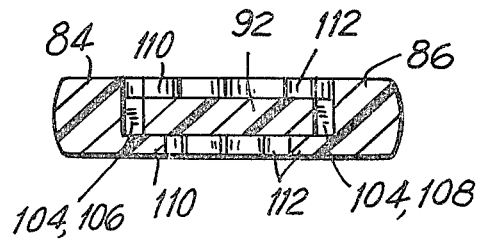
FIG. 11 is a sectional elevation view taken substantially along the line 11—11 of FIG. 9.

It is preferred, as best shown in FIGS. 8 and 9, that the sides of the panel 92 adjacent the arms 84, 86, and the inner edges of the arms 84, 86, should be serrated so that positive engagement of the panel 92 with the arms 84, 86 takes place when the panel 92 is wedged into place. Thus the sides of the panel 92 are provided with serrations 104 and the inner edges of the arms 84, 86 are provided with serrations 106, 108 respectively, as shown in FIG. 8, with the serrations being engaged as shown in FIG. 9. In addition, it is preferred that a plurality of spaced apart tabs 110, 112 be provided along the inner edges of the respective arms 84, 86, on either side of the respective serrations 106, 108, so that the tabs 110, 112 define opposed channels along the inner edges of the arms 84, 86 into which the panel 92 is receivable when the collapsible mounting means, consisting in this case of the thin rectilinear plastic rod 94, is collapsed as shown in FIG. 9. FIGS. 10 and 11 show details of the structural configuration of FIG. 9, specifically with the panel 92 in place and held between the tabs 110, 112 by serrations 104 coacting with serrations 106, 108.

FIGS. 12, 13, 14 and 15 show an embodiment of the invention in which a loop 114 of dental floss, formed by tying a knot 116 in a length of dental floss, is emplaced on a dental floss holder 118 within the scope of the present invention. The bifurcated end 120 of the holder is provided with grooved arms 122, 124 having notched ends 126 and 128 respectively, as best shown in FIG. 15, where a notch 130 is shown in end 126, so that the loop 114 is receivable on the bifurcated end 120 with portions 132 and 134 of the loop 114 extending along in the grooves or channels in the respective arms 122, 124 and the balance of the loop 114 consisting of portion 136 being the working portion of the length of dental floss.

FIG. 13 shows initial emplacement of the loop 114 in the grooves of arms 122 and 124 and under terminal retention lips 138 at the junction 140. Portion 136 of the loop 114 extends in a slack disposition between ends 126 and 128 since the arms 122 and 124 are unstressed. The serrated tongue 142 is not engaged with the opposite tongue 144, i.e. the outer end serration of the serrations 146 of tongue 142 has not received terminal lip 148 of tongue 144.

FIG. 14 shows squeezing or crushing of the handle portion of the holder 118, so that a mode of stressing arms 122 and 124 apart, similar to the action described supra with regard to FIG. 4, has been accomplished. In the interest of brevity, a description of this manipulation will not be repeated. Suffice it to state that fingers 150 move as indicated by arrows 152 so that arms 122, 124 spread apart as indicated by arrows 154, and consequently so that the loop 144 and specifically portion 136 becomes stressed and rectilinear.

In FIG. 14 the lip 148 of tongue 144 engages an inner serration 146. FIG. 15 shows the final disposition of elements with the dental floss holder ready for service.

It thus will be seen that there is provided a holder for dental floss which achieves the various objects of the invention and which is well adapted to meet the conditions of practical use.

As various possible embodiments might be made of the above invention, and as various changes might be made in the embodiments above set forth, it is to be understood that all matter herein described or shown in the accompanying drawings is to be interpreted as illustrative and not in a limiting sense. Thus, it will be understood by those skilled in the art that although preferred and alternative embodiments have been shown and described in accordance with the Patent Statutes, the invention is not limited thereto or thereby.

Having thus described the invention, there is claimed as new and desired to be secured by Letters Patent:

1. A holder for dental floss comprising an oblong handle, said handle having two spaced apart resilient substantially parallel legs, said legs depending from a junction at one end of said handle, said one end of said handle having a bifurcated extension beyond said junction, adjustable means to engage portions of said two legs with each other said adjustable means including at least one pair of opposed tongues, each of said tongues extending inwards towards each other from a leg of the handle and each being substantially perpendicular to its respective leg, at least one of said tongues being provided with serrations, so that said tongues engagingly cooperate with each other to hold the legs toward each other, and thereby to spread apart the arms when the legs are moved towards each other and means mountable on said bifurcated one end of said handle, said mountable means including a length of dental floss.

2. The holder for dental floss of claim 1 in which one tongue is serrated and the other tongue is provided with a terminal lip, said lip engaging the serrations on said one tongue when the legs are moved towards each other.

3. The holder for dental floss of claim 2 in which the lip is offset laterally from the terminus of the other tongue, so that the pair of tongues may be disengaged from each other by laterally displacing the one tongue relative to the other tongue.

4. A holder for dental floss comprising an oblong handle, one end of said handle being bifurcated, a length of dental floss, said length of dental floss extending substantially rectilinearly between proximately the ends of the arms of the bifurcated one end of the handle, each end of said length of dental floss being attached to one of said arms, and means to stress said arms away from each other including a panel, said panel being mounted between the arms on collapsible mounting means and being wedge shaped so that collapsing of the collapsible mounting means wedges said panel towards the one end of the handle and thereby stresses the arms away from each other and said length of dental floss becomes stressed and rectilinear.

5. The holder for dental floss of claim 4 in which the sides of the panel adjacent the arms and the inner edges of the arms are serrated.

6. The holder for dental floss of claim 4 in which a plurality of spaced apart tabs are provided along the inner edges of the arms, said tabs defining opposed channels along the inner edges of the arms into which the panel is receivable when the collapsible mounting means is collapsed.

7. The holder for dental floss of claim 4 in which the collapsible mounting means is a rod, said rod depending from the apex of the panel to the one end of the handle.

* * * * *